(12) United States Patent
Peng

(10) Patent No.: US 9,930,232 B2
(45) Date of Patent: Mar. 27, 2018

(54) COMPUTERIZED TOILET SEAT HAVING IMAGE CAPTURE SYSTEM

(71) Applicant: Shao-Yu Peng, Changhua County (TW)

(72) Inventor: Shao-Yu Peng, Changhua County (TW)

( * ) Notice: Subject to any disclaimer, the term of this patent is extended or adjusted under 35 U.S.C. 154(b) by 8 days.

(21) Appl. No.: 15/352,556

(22) Filed: Nov. 15, 2016

(65) Prior Publication Data

US 2017/0142306 A1    May 18, 2017

(30) Foreign Application Priority Data

Nov. 16, 2015 (TW) .............................. 104137773 A

(51) Int. Cl.
| | | |
|---|---|---|
| *H04N 5/225* | (2006.01) | |
| *A47K 13/24* | (2006.01) | |
| *A61B 5/00* | (2006.01) | |
| *H04N 5/232* | (2006.01) | |
| *A47K 7/08* | (2006.01) | |

(52) U.S. Cl.
CPC ............ *H04N 5/2253* (2013.01); *A47K 13/24* (2013.01); *A61B 5/0077* (2013.01); *A61B 5/742* (2013.01); *H04N 5/23203* (2013.01); *H04N 5/23254* (2013.01); *H04N 5/23293* (2013.01); *H04N 5/23296* (2013.01); *A47K 7/08* (2013.01)

(58) Field of Classification Search
CPC .................................................... H04N 5/2253
See application file for complete search history.

(56) References Cited

U.S. PATENT DOCUMENTS

| 9,428,898 | B1* | 8/2016 | Clements | .................. E03D 9/08 |
|---|---|---|---|---|
| 9,477,317 | B1* | 10/2016 | Clements | ................ G06F 3/017 |
| 9,756,297 | B1* | 9/2017 | Clements | ................ H04N 7/185 |
| 9,822,519 | B2* | 11/2017 | Hall | .......................... E03D 9/08 |
| 9,828,755 | B1* | 11/2017 | Clements | .................. E03D 9/08 |
| 9,834,917 | B2* | 12/2017 | Moore | .................... E03D 1/012 |

(Continued)

FOREIGN PATENT DOCUMENTS

| TW | M427400 U1 | 4/2012 |
|---|---|---|
| WO | 03/102315 A1 | 12/2003 |

OTHER PUBLICATIONS

Office Action of corresponding TW application No. 104137773, published on Apr. 13, 2016.

*Primary Examiner* — James Pontius
(74) *Attorney, Agent, or Firm* — Bruce Stone LLP; Joseph A. Bruce

(57) ABSTRACT

A computerized toilet seat having an image capture system includes a toilet seat body; a positioning auxiliary device, disposed on the toilet seat body and having a main body and a connecting member; an image capture unit, coupled to the connecting member and having an optical positioning element, a first space being defined between the optical positioning element and the buttocks; and a manipulator, electrically connected to the image capture unit for operating the positioning auxiliary device. The manipulator controls the image capture unit to capture an image of the buttocks. After capturing the image, the manipulator calculates and adjusts a relative position of the buttocks and the connecting member through the optical positioning element, and the image of the buttocks is displayed on the manipulator according to a relative position of the first space and the buttocks, and operation information of the positioning auxiliary device is provided to the manipulator.

6 Claims, 5 Drawing Sheets

(56) References Cited

U.S. PATENT DOCUMENTS

| | | | |
|---|---|---|---|
| 2011/0083264 A1* | 4/2011 | Gunderson | A47K 17/00 4/661 |
| 2015/0000026 A1* | 1/2015 | Clements | G06F 3/013 4/443 |
| 2015/0020301 A1* | 1/2015 | Moore | A47K 13/242 4/420 |
| 2015/0059076 A1* | 3/2015 | Tiagai | G06T 1/0014 4/447 |
| 2017/0260728 A1* | 9/2017 | Hall | E03D 9/08 |
| 2017/0303901 A1* | 10/2017 | Sekine | A61B 10/0038 |
| 2017/0332852 A1* | 11/2017 | Shimon | A47K 13/225 |

\* cited by examiner

COMPUTERIZED TOILET SEAT HAVING IMAGE CAPTURE SYSTEM

CROSS REFERENCE TO RELATED APPLICATION

This application claims the benefit of priority to TW 104137773, filed on Nov. 16, 2015 with the Intellectual Property Office of the Republic of China, Taiwan, the entire specification of which is incorporated herein by reference.

FIELD OF THE INVENTION

The present invention relates to a computerized toilet seat having an image capture system, and more particularly to a computerized toilet seat having an image capture system to capture an image of the user's buttocks or genitals in cooperation with a cleaning unit to clean the human body and to analyze the image of the excrement to obtain health information.

BACKGROUND OF THE INVENTION

The toilet is an essential daily article for physiological needs. Like electronic products, the industry would like to further design or improve the toilet in order to obtain people's preferences, such as a computerized toilet seat for the user to clean his/her buttocks after using the toilet. Although these improved toilet devices have been seen everywhere, few toilet devices have other ancillary functions.

For example, a conventional computerized toilet seat cleans the user's buttocks (e.g., the anus) by washing the anus, but the body of each user is different in size and sex, and even a sitting posture is different. Sometimes, there is still a little excrement adhered to the anus, causing distress to the user.

In addition, one of the ways to know the human health is to observe his/her excreta. But, people generally observe their own excreta after using the toilet by the naked eyes to get an initial inspection. This makes it difficult to obtain a more accurate understanding of physiological conditions. If people want more precise information, they must go to a medical institutions for medical inspections, which is quite inconvenient.

Based on the foregoing, the inventor of the present invention has devoted himself based on his many years of practical experiences to solve these problems and develop a computerized toilet seat having an image capture system to obtain a better cleaning effect through an image capture device to capture the image of the user's buttocks. Besides, the user can accurately understand his/her health after using the toilet via his/her excrement.

SUMMARY OF THE INVENTION

The primary object of the present invention is to provide a computerized toilet seat having an image capture system. Through an image capture unit to capture an image of the buttocks of a user for cleaning the buttocks or the genitals to provide a better cleaning effect.

Another object of the present invention is to provide a computerized toilet seat having an image capture system, wherein the image capture unit has a horizontal rotation function to capture an image of the user's excrement for the user to know his/her health.

In order to achieve the aforesaid object, the computerized toilet seat having an image capture system of the present invention comprises a toilet seat body, a positioning auxiliary device, an image capture unit, a manipulator, and an assembled fitting. The positioning auxiliary device is disposed on the toilet seat body. The positioning auxiliary device has a main body and a connecting member connected with the main body. The image capture unit is coupled to the connecting member and has an optical positioning element. A first space is defined between the optical positioning element and the buttocks of a user. The manipulator is electrically connected to the image capture unit for operating the positioning auxiliary device. Wherein, the manipulator is used to control the image capture unit to capture an image of the user's buttocks or genitals. After capturing the image, the manipulator calculates and adjusts a relative position of the user's buttocks and the connecting member through the optical positioning element, and the image of the user's buttocks is displayed on the manipulator in accordance with a relative position of the first space and the user's buttocks, and operation information of the positioning auxiliary device is provided to the manipulator. The assembled fitting has an engaging portion, enabling the assembled fitting to be connected to the connecting member.

Thereby, the expected effects of the present invention are described as below:

1. The image capture unit of the present invention cooperates with the positioning auxiliary unit. When in use, the image capture unit aims at the user's buttocks or the genitals to provide a better cleaning effect.

2. The image capture unit of the present invention has a drive device to rotate about its axis. Thus, the image capture unit provides a rotation function. Through the function, the image capture unit is able to capture an image of the user's excrement for the user to know his/her health.

The connecting member of the present invention has a male or female engaging portion. Besides, the present invention provides multiple assembled fittings, so that the user can replace the assembled fittings as desired to enhance the product value.

The assembled fitting is provided with a chip analysis unit which is able to discriminate fecal matter for providing health information.

DESCRIPTION OF THE PREFERRED EMBODIMENTS

In order to understand the present invention, embodiments of the present invention will now be described, by way of example only, with reference to the accompanying drawings.

Figure 1:
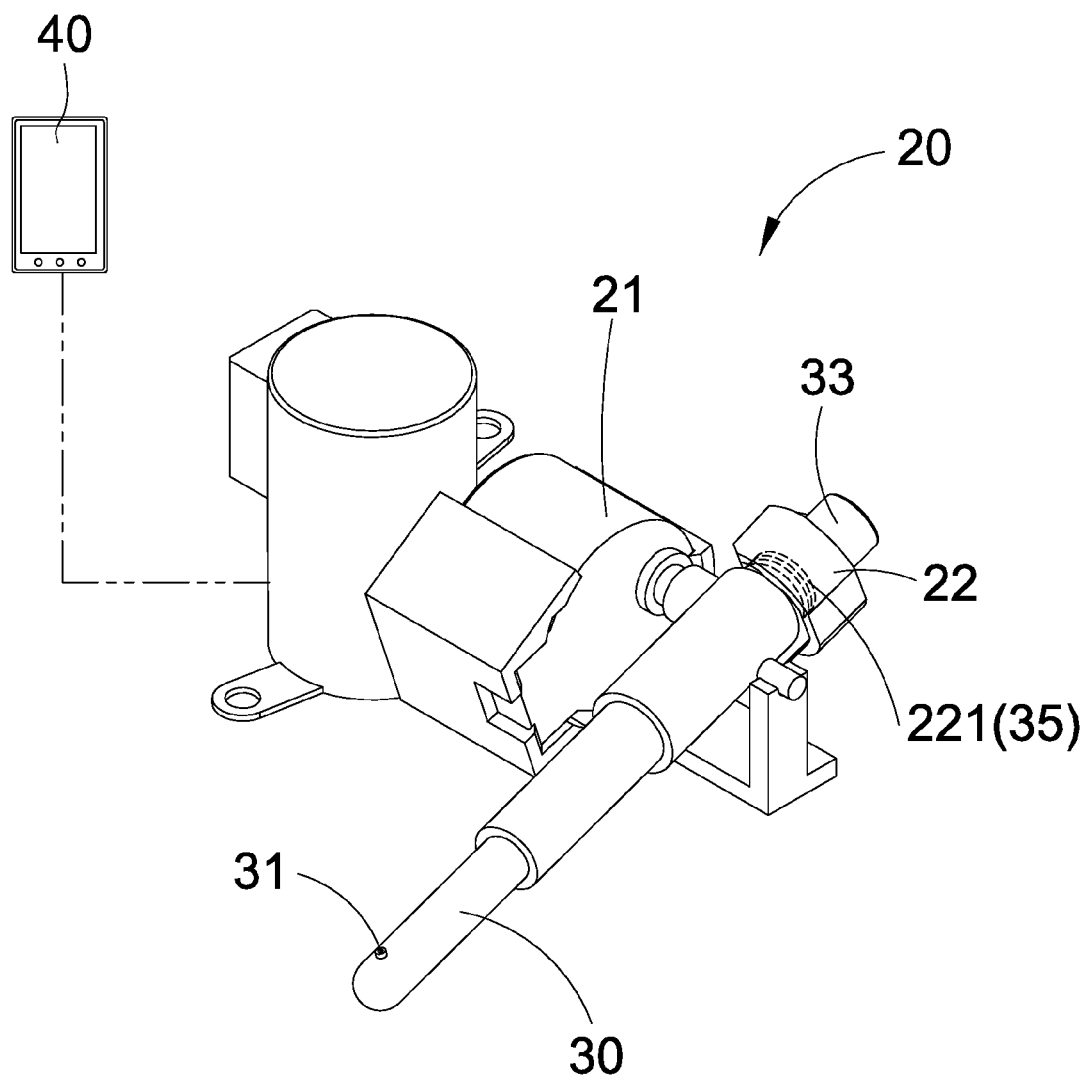
FIG. 1 is a perspective view of the present invention.
Figure 2:
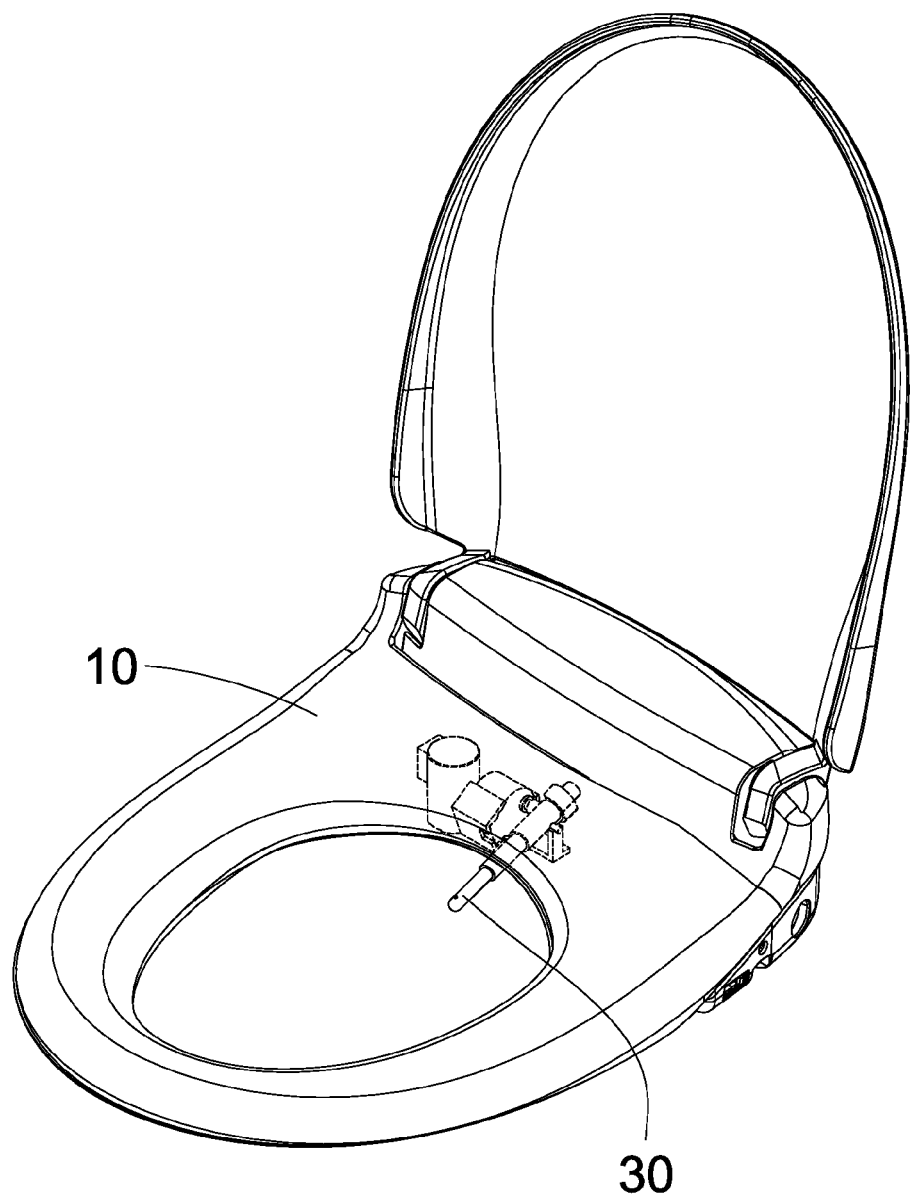
FIG. 2 is a perspective view of the present invention when in use.

As shown in FIG. 1 and FIG. 2, a computerized toilet seat having an image capture system according to an embodiment of the present invention comprises a toilet seat body 10, a positioning auxiliary device 20, an image capture unit 30, and a manipulator 40. The positioning auxiliary device 20 is disposed on the toilet seat body 10. The positioning auxiliary device 20 has a main body 21 and a connecting member 22 connected with the main body 21. The image capture unit 30 is coupled to the connecting member 22, and has an optical positioning element 31. A first space 32 is defined between the optical positioning element 31 and the buttocks of a user. The manipulator 40 is electrically connected to the image capture unit 30 for operating the positioning auxiliary device 20.

Figure 3:
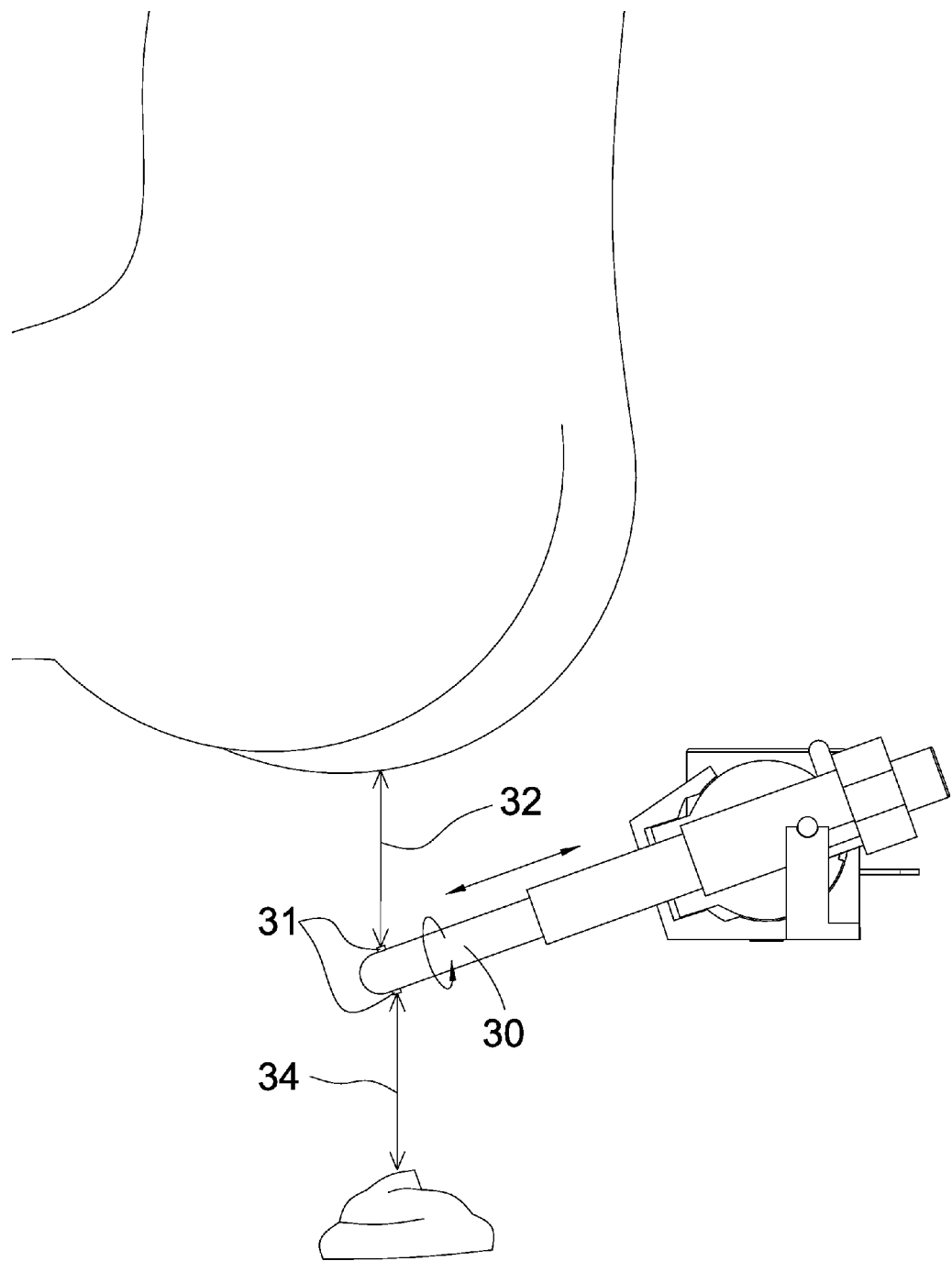
FIG. 3 is a schematic view of the present invention when in use, showing that the image capture unit can be moved back and forth.

Referring to FIG. 3, the manipulator 40 is used to control the image capture unit 30 to capture an image of the user's buttocks or genitals. After capturing the image, the manipulator 40 calculates and adjusts the relative position of the connecting member 22 and the user's buttocks through the optical positioning element 31, and the image of the user's buttocks is displayed on the manipulator 40 in accordance with the relative position of the first space 32 and the user's buttocks, and the operation information of the positioning auxiliary device 20 is provided to the manipulator 40.

Figure 4:
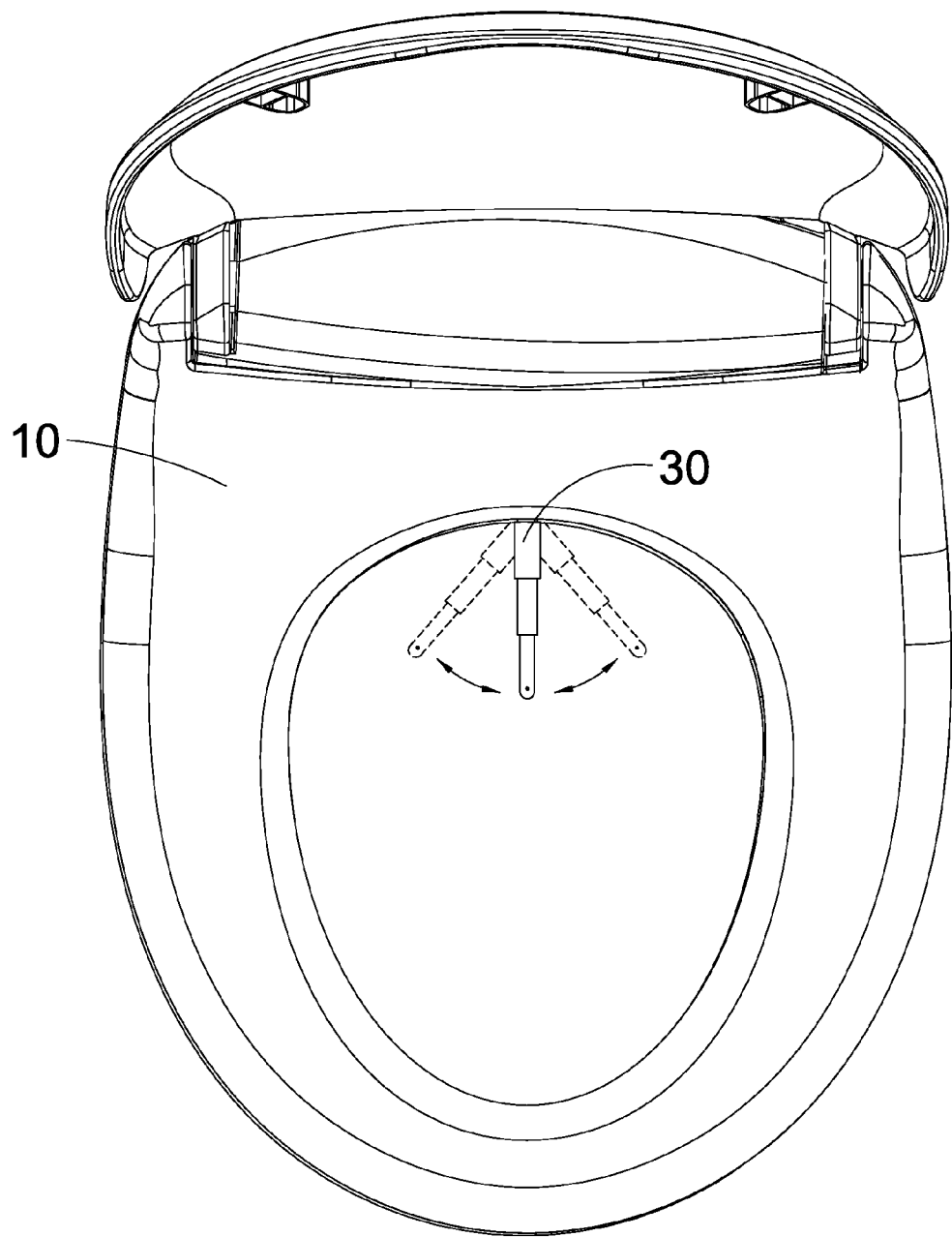
FIG. 4 is a schematic view of the present invention when in use, showing that the image capture unit can be moved left and right.

Through the aforesaid mechanism, the use and the expected effects of the present invention are described hereinafter. Referring to FIG. 3 and FIG. 4, the body 21 has a drive device for driving the positioning auxiliary device 20, such that the positioning auxiliary device 20 can move left and right as well as back and forward to adjust the focus. The manipulator 40 calculates the first space 32 formed between the optical positioning element 31 and the user's buttocks and adjusts the focs between the user's buttocks and the image capture unit 30. The optical positioning element 31 generates a light source to illuminate the user's buttocks for the focus of the image capture unit 30. After that, the manipulator 40 drives the position auxiliary device 20 to adjust the position of the connecting member 22 according to the feature (such as the anus and the genitals) of the user's buttocks, and the feature of the user's buttocks is displayed on the manipulator 40, and the operation information of the positioning auxiliary device 20 is provided to the manipulator 40. The user activates the cleansing device (not shown) according to the instructions to clean the user's buttocks in cooperation with the manipulator 40 to get a better cleaning effect. Furthermore, the manipulator 40 has a storage unit and a transmission unit. The storage unit is used to record the captured image. The transmission unit is used for transmission of the captured image. For example, the captured image is transmitted to a family doctor, a hospital, a medical laboratory, etc., for inspections by a professional.

Since it is possible to extract the health information from excrement, for example, hemoglobin of bloody stools and excreta can be used to judge whether anemia or *Escherichia coli* is present or not and whether colorectal cancer is present or not. Thus, many people go to medical centers or test centers for inspection of excrement. However, the conventional method requires a special time to examine the excrement. If the diet or work and rest are irregular before the inspection, it may cause a problem that the test data may be incorrect. Therefore, the image capture unit 30 of the present invention has a drive device 33 able to rotate about its axis. A second space 34 is defined between the optical positioning element 31 and the user's excrement. The relative position of the second space 34 and the user's excrement is displayed on the manipulator 40. Thereby, the image capture unit 30 is adjusted to focus on the excrement and capture an image of the excrement. The manipulator 40 has a storage unit (whether wired or wireless) to record the captured image and provides the captured image to the test center or medical institution for analysis. In this way, the user can know his/her own health and reduce the time going to the medical institutions for inspection, and the incorrect test data can be lowered.

Other arrangements of the connecting member 22 of the present invention may be employed. In other words, the user can connect an assembled fitting 50 to the connecting member 22 as required. For example, the connecting member 22 and the image capture unit 30 respectively have male and female engaging portions 221, 35 for the connection of the connecting member 22 and the image capture unit 30. The engaging portions 221, 35 may be quick-release connectors, bolts and nuts, and the like, so that they can be connected quickly. The user may replace the assembled fitting 50 with a cleaning device, a spray device, etc., to facilitate the convenience of the present invention.

Figure 5:
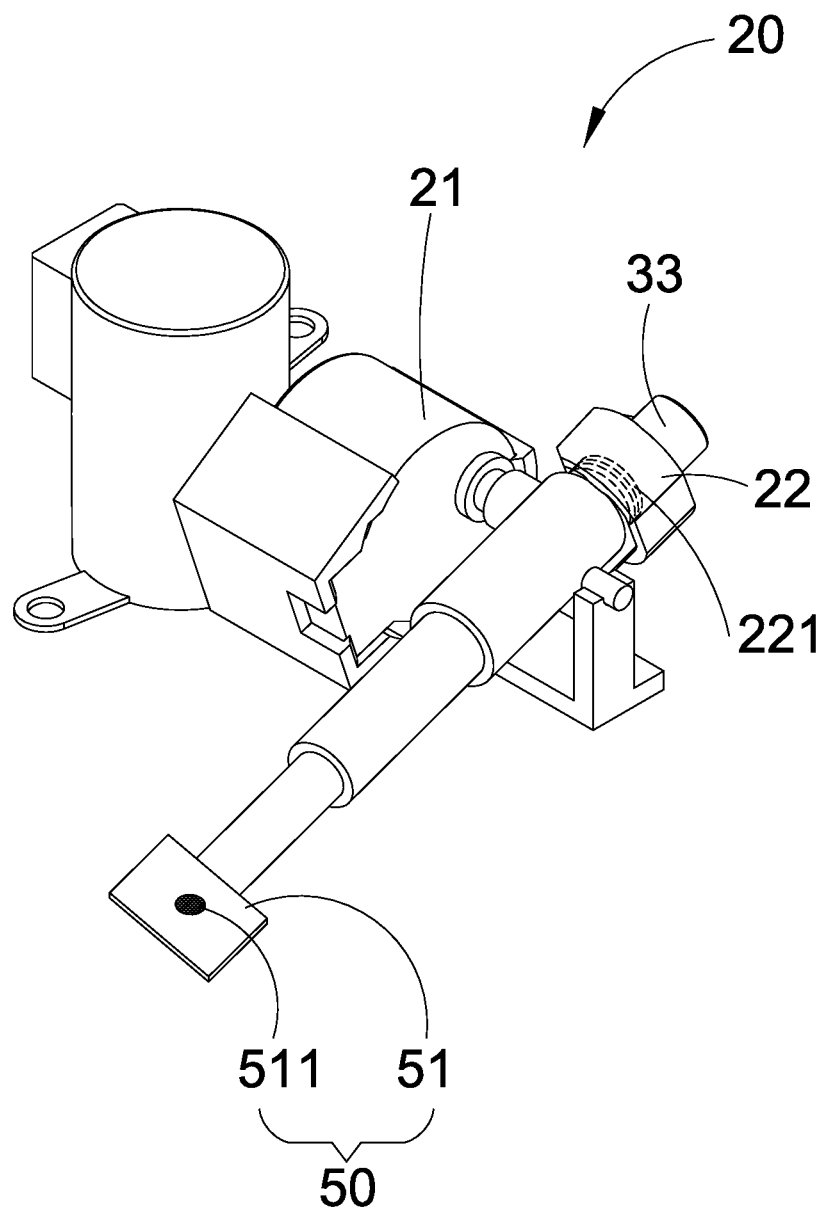
FIG. 5 is a schematic view of the present invention in another use state.

Referring to FIG. 5, in order to collect the user's excrement conveniently, the assembled fitting 50 of the present invention has a carrying portion 51. The carrying portion 51 is provided with a chip analysis unit 511 for discriminating fecal matter. The chip analysis unit 511 can collect the excretions for inspection, such as *Escherichia coli*, bloody stools, etc., so that the user need not dig through excrement in a bedpan, and the uncomfortable feeling caused by the feces and excretions can be avoided.

In summary, the image capture unit 30 of the present invention cooperates with the positioning auxiliary unit 20 to assist in displacement and adjusting the focal for displaying the user's buttocks on the manipulator 40. The user can clean the buttocks or capture the image of the excrement according to the operation instructions. The present invention not only provides a better cleaning effect for the buttocks but also provides a health management. Furthermore, the connecting member 22 has a good replaceability. The assembled fitting 50 can be replaced according to the demand.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A computerized toilet seat having an image capture system, comprising:
   a toilet seat body;
   a positioning auxiliary device, disposed on the toilet seat body, the positioning auxiliary device having a main body and a connecting member connected with the main body;
   an image capture unit, coupled to the connecting member and having an optical positioning element, a first space being defined between the optical positioning element and the buttocks of a user;
   a manipulator, electrically connected to the image capture unit for operating the positioning auxiliary device;
   wherein the manipulator is used to control the image capture unit to capture an image of the user's buttocks or genitals, after capturing the image, the manipulator calculates and adjusts a relative position of the user's buttocks and the connecting member through the optical positioning element, and the image of the user's buttocks is displayed on the manipulator in accordance with a relative position of the first space and the user's buttocks, and operation information of the positioning auxiliary device is provided to the manipulator;

an assembled fitting, the assembled fitting having an engaging portion for the assembled fitting to be connected to the connecting member.

2. The computerized toilet seat having an image capture system as claimed in claim 1, wherein the image capture unit has a drive device able to rotate about its axis, a second space is defined between the optical positioning element and the user's excrement, and a relative position of the second space and the user's excrement is displayed on the manipulator.

3. The computerized toilet seat having an image capture system as claimed in claim 1 or 2, wherein the manipulator has a storage unit and a transmission unit, the storage unit is used to record the captured image, and the transmission unit is used for transmission of the captured image.

4. The computerized toilet seat having an image capture system as claimed in claim 1, wherein the connecting member and the image capture unit have male and female engaging portions respectively, through engagement of the male and female engaging portions, the image capture unit is connected to the connecting member.

5. The computerized toilet seat having an image capture system as claimed in claim 1, wherein the assembled fitting has a carrying portion for collecting the user's excrement.

6. The computerized toilet seat having an image capture system as claimed in claim 5, wherein the carrying portion is provided with a chip analysis unit for discriminating the user's excrement.

* * * * *